United States Patent
Castaneda et al.

(10) Patent No.: US 10,806,499 B2
(45) Date of Patent: Oct. 20, 2020

(54) UNIVERSAL ORTHOPEDIC CLAMP

(71) Applicants: Javier E. Castaneda, Miami, FL (US); Roberto Augusto Miki, Pinecrest, FL (US); Ernesto Hernandez, Weston, FL (US); John William Box, Coral Gables, FL (US); Scott M. Whitten, Sunrise, FL (US)

(72) Inventors: Javier E. Castaneda, Miami, FL (US); Roberto Augusto Miki, Pinecrest, FL (US); Ernesto Hernandez, Weston, FL (US); John William Box, Coral Gables, FL (US); Scott M. Whitten, Sunrise, FL (US)

( * ) Notice: Subject to any disclaimer, the term of this patent is extended or adjusted under 35 U.S.C. 154(b) by 0 days.

(21) Appl. No.: 16/155,567

(22) Filed: Oct. 9, 2018

(65) Prior Publication Data

US 2019/0105092 A1 Apr. 11, 2019

Related U.S. Application Data

(60) Provisional application No. 62/570,390, filed on Oct. 10, 2017.

(51) Int. Cl.
*A61B 17/88* (2006.01)
*A61B 17/60* (2006.01)
(Continued)

(52) U.S. Cl.
CPC .......... *A61B 17/8866* (2013.01); *A61B 17/60* (2013.01); *A61B 2017/0069* (2013.01); *A61B 2017/564* (2013.01)

(58) Field of Classification Search
CPC ........ A61B 17/80–8004; A61B 17/808; A61B 17/8061–8076; A61B 17/8841; A61B 17/8866; A61B 17/8872; A61B 17/7047; A61B 17/7056; A61B 17/707; A61B 17/64–6491; A61B 17/88; Y10T 24/344;
(Continued)

(56) References Cited

U.S. PATENT DOCUMENTS 842,007 A * 1/1907 Parker ..................... B25B 5/006
269/45
852,180 A * 4/1907 Hoffman .............. A47C 21/022
24/72.5
(Continued)

FOREIGN PATENT DOCUMENTS

| CN | 103976773 | 8/2014 |
|---|---|---|
| CN | 106037882 A | 10/2016 |
| EP | 2436324 A1 | 4/2012 |

OTHER PUBLICATIONS

"Innovations in Orthopedic Instruments" (INNOMED) Aug. 2016.
International Search Report and Written Opinion of Application No. PCT/US18/053927 dated Dec. 21, 2018.

*Primary Examiner* — Eduardo C Robert
*Assistant Examiner* — Michelle C Eckman
(74) *Attorney, Agent, or Firm* — Gordon & Jacobson, P.C.

(57) ABSTRACT

A bone clamping device includes a pair of clamps mounted on a clamp connector. Each clamp has a variable size opening that varies in size transverse to the clamp connector. At least one clamp is longitudinally and angularly displaceable relative to the other along the clamp connector. The clamps are preferably made from a plastic and the clamp connector is preferably made from metal.

31 Claims, 8 Drawing Sheets

(51) Int. Cl.
  *A61B 17/56* (2006.01)
  *A61B 17/00* (2006.01)

(58) Field of Classification Search
  CPC .......... Y10T 24/3435; Y10T 24/44385; Y10T 24/44402; Y10T 24/44504
  USPC ............................ 606/324; 269/45, 143, 249
  See application file for complete search history.

(56) References Cited

U.S. PATENT DOCUMENTS

| | | | | |
|---|---|---|---|---|
| 1,766,546 A * | 6/1930 | Roos | ........................ | G01B 3/24 33/558.1 |
| 1,782,752 A * | 11/1930 | Weisler | .................. | B25B 13/30 81/118 |
| 1,985,108 A * | 12/1934 | Rush | .................. | A61B 17/8866 606/86 R |
| 2,168,257 A * | 8/1939 | Farmer | .................. | B25B 5/102 269/171.5 |
| 2,190,143 A * | 2/1940 | Barnes | .................... | H01R 4/64 238/14.13 |
| 2,225,875 A * | 12/1940 | Liebmann | ............ | A47C 21/022 24/72.5 |
| 2,362,957 A * | 11/1944 | Hackett | .............. | A61B 17/8861 606/86 R |
| 2,427,128 A * | 9/1947 | Ettinger | ............. | A61B 17/8866 606/86 R |
| 2,460,470 A * | 2/1949 | Rogers | .................. | A61B 17/2812 606/86 R |
| 2,583,896 A * | 1/1952 | Siebrandt | .............. | A61B 17/808 606/86 R |
| 2,631,585 A * | 3/1953 | Siebrandt | ........... | A61B 17/8866 606/86 R |
| 2,669,958 A * | 2/1954 | Sweeney | ............ | B23K 37/0426 269/45 |
| 2,913,792 A * | 11/1959 | Land | .................... | A47G 25/485 24/332 |
| 3,477,429 A * | 11/1969 | Sampson | ........... | A61B 17/8866 606/86 R |
| 3,604,069 A * | 9/1971 | Jensen | .................... | A44B 99/00 24/332 |
| 3,609,638 A * | 9/1971 | Darrey | ............... | H01R 13/6392 439/369 |
| 3,727,272 A * | 4/1973 | Rhodes | .................. | A41H 15/00 24/300 |
| 3,736,629 A * | 6/1973 | Blake | ...................... | B25B 5/103 24/514 |
| RE27,986 E * | 4/1974 | Jensen | ................... | A44B 99/00 24/332 |
| 4,187,840 A * | 2/1980 | Watanabe | ............ | A61B 17/808 606/86 R |
| 4,611,582 A | 9/1986 | Duff | | |
| 5,133,342 A * | 7/1992 | Seaton | .................... | A61B 17/58 602/39 |
| 5,302,039 A * | 4/1994 | Omholt | ................. | E04B 2/7401 403/218 |
| 5,312,403 A * | 5/1994 | Frigg | .................. | A61B 17/2833 606/54 |
| 5,342,364 A * | 8/1994 | Mikhail | ............. | A61B 17/2812 606/79 |
| 5,578,032 A * | 11/1996 | Lalonde | ............. | A61B 17/282 606/205 |
| 5,645,548 A * | 7/1997 | Augsburger | ....... | A61B 17/6408 606/54 |
| 5,797,919 A * | 8/1998 | Brinson | ............. | A61B 17/8866 606/105 |
| 5,885,298 A * | 3/1999 | Herrington | ........ | A61B 17/1767 606/88 |
| 5,951,556 A | 9/1999 | Faccioli et al. | | |
| 6,171,307 B1 | 1/2001 | Orlich | | |
| 6,171,308 B1 | 1/2001 | Bailey et al. | | |
| 6,221,072 B1 | 4/2001 | Termaten | | |
| 6,287,307 B1 * | 9/2001 | Abboudi | ............ | A61B 17/8061 606/105 |
| 6,315,780 B1 * | 11/2001 | Lalonde | ............... | A61B 17/282 606/105 |
| 6,387,097 B1 * | 5/2002 | Alby | .................. | A61B 17/7032 606/277 |
| 6,443,955 B1 * | 9/2002 | Ahrend | .............. | A61B 17/8866 606/103 |
| 6,579,296 B1 * | 6/2003 | Macey | .................. | A61B 17/808 606/86 R |
| 6,605,088 B1 * | 8/2003 | St. Onge | ................... | A61F 5/05 606/54 |
| 6,702,824 B2 * | 3/2004 | Maroney | .................... | A61F 2/40 606/99 |
| 7,147,639 B2 | 12/2006 | Berki et al. | | |
| 7,881,771 B2 | 2/2011 | Koo et al. | | |
| 8,192,449 B2 * | 6/2012 | Maier | ................ | A61B 17/8866 600/426 |
| 8,230,863 B2 * | 7/2012 | Ravikumar | ........... | A61B 90/57 128/845 |
| 8,231,623 B1 * | 7/2012 | Jordan | .................... | A61B 17/64 606/250 |
| 8,388,619 B2 | 3/2013 | Mullaney | | |
| 8,579,950 B1 * | 11/2013 | Jordan | ................ | A61B 17/8866 606/324 |
| 8,685,037 B1 * | 4/2014 | Jordan | ............... | A61B 17/8866 606/105 |
| 9,131,974 B1 * | 9/2015 | Boyer | ................ | A61B 17/1767 |
| 9,204,908 B2 | 12/2015 | Buttermann | | |
| 9,402,746 B2 * | 8/2016 | Boyer | .................... | A61F 2/4657 |
| 9,550,277 B1 * | 1/2017 | Williams | ........... | A61B 17/8866 |
| 9,554,813 B2 * | 1/2017 | Clever | .............. | A61B 17/1767 |
| 9,572,590 B2 * | 2/2017 | Singhal | ................ | A61B 17/175 |
| 9,943,337 B2 * | 4/2018 | Muniz | ............... | A61B 17/6466 |
| 10,034,679 B1 * | 7/2018 | Boyer | ............... | A61B 17/1767 |
| 10,179,001 B2 * | 1/2019 | Hashmi | ............... | A61B 17/3403 |
| 2001/0053911 A1 * | 12/2001 | Hehli | ................. | A61B 17/8866 606/53 |
| 2003/0004513 A1 * | 1/2003 | Guzman | ............ | A61B 17/1635 606/62 |
| 2003/0080267 A1 * | 5/2003 | Eslick | ..................... | F16B 2/065 248/229.1 |
| 2003/0149430 A1 * | 8/2003 | Ferrante | ............... | A61B 17/645 606/59 |
| 2004/0055429 A1 * | 3/2004 | Winkler | .................... | B25B 7/02 81/367 |
| 2004/0232608 A1 * | 11/2004 | Wong | ...................... | B25B 5/006 269/249 |
| 2005/0149028 A1 | 7/2005 | Birkbeck et al. | | |
| 2006/0116679 A1 * | 6/2006 | Lutz | ...................... | A61B 17/02 606/86 B |
| 2008/0009871 A1 * | 1/2008 | Orbay | ................ | A61B 17/1728 606/70 |
| 2008/0221625 A1 * | 9/2008 | Hufner | ............... | A61B 17/1757 606/324 |
| 2009/0024127 A1 * | 1/2009 | Lechner | ............... | A61L 31/126 606/53 |
| 2009/0030462 A1 * | 1/2009 | Buttermann | ....... | A61B 17/7047 606/249 |
| 2009/0062869 A1 * | 3/2009 | Claverie | ............ | A61B 90/50 606/324 |
| 2009/0118775 A1 * | 5/2009 | Burke | .................... | A61B 17/08 606/324 |
| 2009/0187217 A1 * | 7/2009 | Weiman | ............ | A61B 17/7052 606/257 |
| 2011/0066151 A1 * | 3/2011 | Murner | ............. | A61B 17/6466 606/54 |
| 2011/0106183 A1 * | 5/2011 | Dell'oca | ............ | A61B 17/282 606/86 B |
| 2011/0118750 A1 * | 5/2011 | Wu | ........................ | A61B 34/20 606/130 |
| 2011/0137353 A1 * | 6/2011 | Buttermann | ........ | A61B 17/7001 606/305 |
| 2011/0257657 A1 | 10/2011 | Turner et al. | | |
| 2011/0270314 A1 * | 11/2011 | Mueller | ................ | A61B 17/704 606/264 |

(56) References Cited

U.S. PATENT DOCUMENTS

| | | | |
|---|---|---|---|
| 2012/0093575 A1* | 4/2012 | Busch | A61B 17/6466 403/154 |
| 2012/0130384 A1* | 5/2012 | Henderson | A61B 17/151 606/87 |
| 2012/0221059 A1* | 8/2012 | Mollman | A61B 17/7074 606/277 |
| 2012/0271366 A1* | 10/2012 | Katrana | A61B 17/282 606/86 R |
| 2013/0025093 A1* | 1/2013 | Liao | B25B 5/10 24/514 |
| 2013/0116733 A1* | 5/2013 | Stoll, Jr. | A61B 17/808 606/282 |
| 2013/0131738 A1* | 5/2013 | Powell | A61B 17/84 606/324 |
| 2013/0165939 A1* | 6/2013 | Ries | A61B 17/8863 606/88 |
| 2013/0261674 A1* | 10/2013 | Fritzinger | A61B 17/808 606/286 |
| 2013/0345762 A1* | 12/2013 | Dell'oca | A61B 17/8866 606/324 |
| 2014/0094818 A1* | 4/2014 | Wallace | A61B 17/8866 606/96 |
| 2015/0031985 A1* | 1/2015 | Reddy | A61B 5/061 600/424 |
| 2015/0032158 A1* | 1/2015 | Khajavi | A61B 17/7002 606/246 |
| 2015/0209093 A1* | 7/2015 | Dallis | A61B 17/8023 606/281 |
| 2015/0209939 A1* | 7/2015 | Chi-Fu | B25B 5/003 269/45 |
| 2016/0015430 A1* | 1/2016 | Buttermann | A61B 17/7032 606/276 |
| 2016/0128730 A1* | 5/2016 | Zhang | A61B 17/68 606/86 R |
| 2016/0249952 A1* | 9/2016 | Gerold | A61B 17/6416 606/57 |
| 2016/0346097 A1* | 12/2016 | Boyer | A61B 17/8802 |
| 2016/0374694 A1* | 12/2016 | Haberman | A61B 17/1635 606/80 |
| 2017/0086989 A1* | 3/2017 | Boyer | B25B 5/101 |
| 2017/0113330 A1* | 4/2017 | Williams | B25B 7/04 |
| 2017/0156757 A1* | 6/2017 | Muniz | A61B 17/6425 |
| 2017/0156892 A1* | 6/2017 | Roose | A61F 2/4609 |
| 2017/0252069 A1* | 9/2017 | Muniz | A61B 17/6483 |
| 2017/0281202 A1* | 10/2017 | Hampp | A61B 17/1767 |
| 2017/0296248 A1* | 10/2017 | Paulisch | A61B 17/8866 |
| 2018/0092667 A1* | 4/2018 | Heigl | A61B 17/2833 |
| 2018/0110542 A1* | 4/2018 | DeVasConCellos | A61B 17/844 |
| 2018/0132909 A1* | 5/2018 | Hackathorn, II | A61B 17/7065 |
| 2018/0168699 A1* | 6/2018 | Goel | A61B 17/7032 |
| 2018/0168707 A1* | 6/2018 | Shariati | A61B 17/8866 |
| 2018/0193071 A1* | 7/2018 | Errico | A61B 17/8028 |
| 2019/0008564 A1* | 1/2019 | Beyer | A61B 17/0206 |
| 2019/0046235 A1* | 2/2019 | Waisman | A61B 17/282 |
| 2019/0105092 A1* | 4/2019 | Castaneda | A61B 17/8866 |
| 2019/0160632 A1* | 5/2019 | Chang | B25B 5/003 |
| 2019/0183531 A1* | 6/2019 | Miller | A61B 17/645 |
| 2019/0328434 A1* | 10/2019 | Slocum | A61B 17/8866 |

* cited by examiner

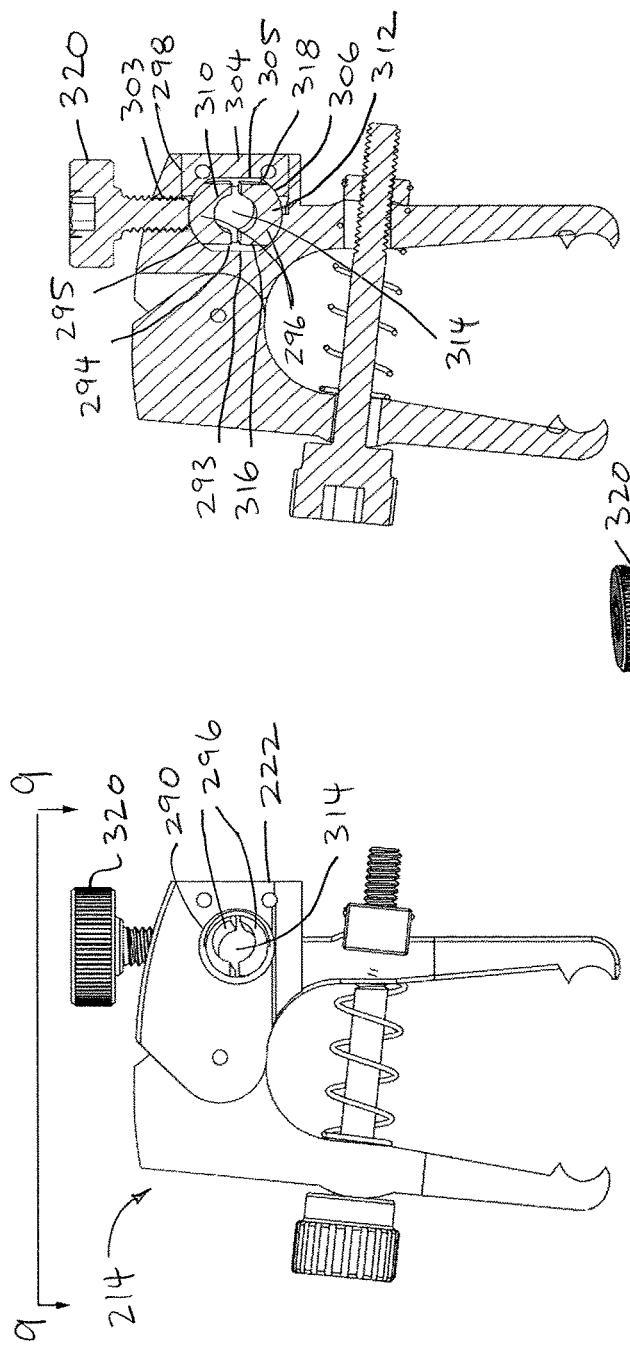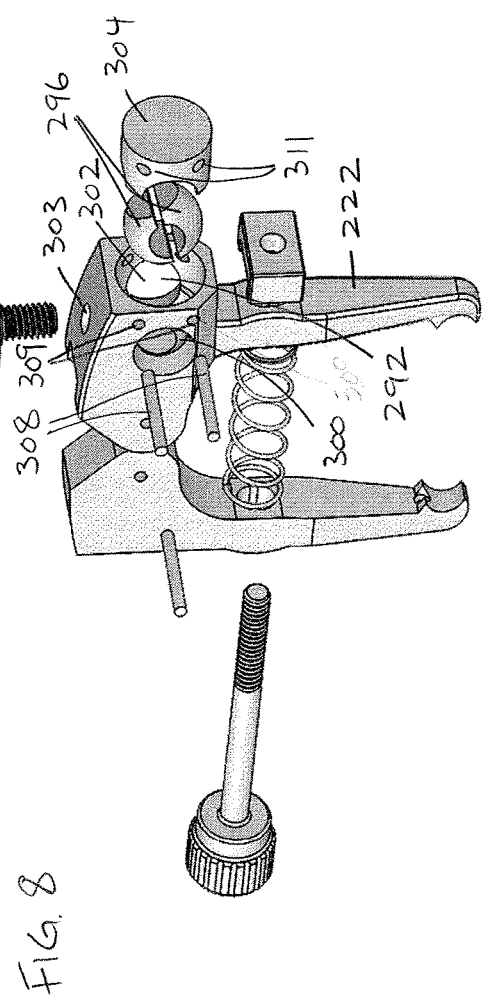

UNIVERSAL ORTHOPEDIC CLAMP

CROSS-REFERENCE TO RELATED APPLICATION

This application claims benefit of U.S. provisional application Ser. No. 62/570,390, filed Oct. 10, 2017, the entire contents of which are hereby incorporated herein by reference.

BACKGROUND OF THE INVENTION

1. Field of the Invention

The present invention relates to orthopedic surgical instruments. More particularly this invention relates to clamps that temporarily hold bone portions of one or more bone in place during an orthopedic surgery.

2. State of the Art

Bone fractures require reduction and fixation. Reduction is the process of remedying a dislocation or fracture by returning the affected part of the body to its normal position. Fixation is the stable maintenance of the fracture in the reduced position during the healing process. Certain fractures need to be reduced and fixed surgically. The surgeon manipulates the various dislocated fragments in position, and then screws a rigid bone plate to the bone to stabilize the fracture.

Reducing the fracture can be a difficult process, as it can be challenging to retain the various elements of the bone in a desired configuration while positioning and securing the bone plate to the bone. Clamping is commonly used to provide temporary fixation without compromising the bone. The clamps are generally either forceps-style clamps or C-clamps.

Forceps-style clamps include two clamping surfaces mounted on arms coupled relative to a pivot point and are exemplified by the clamp described in U.S. Pat. No. 5,797,919 to Briton. One significant disadvantage of such clamps is that the arms and handle of the instrument approach the surgical wound transverse the direction of the clamping force. Thus, positioning the clamping surfaces around the bone is difficult and the surgical wound may need to be opened up more than necessary for clamp access. In addition, given the transverse extension of the handle, there is significant opportunity for the handle to be bumped by the surgeon during the procedure or even for the tissue surrounding the surgical wound to apply sufficient force to the handle to cause inadvertent movement of the clamp and move the plate relative to the bone.

C-clamps have clamping surfaces that longitudinally translate relative to each other, rather than pivot relative to each other. For example, U.S. Pat. No. 4,187,840 to Watanabe discloses a C-shaped bone clamp that overcome some of the problems of forceps-style clamps. The handle extends up and out of the wound rather than transverse to it. Yet, the upwardly extending handle remains in the way of the surgeon, obstructing the portion of the plate held by the arms and limiting access for drilling holes in the plate.

SUMMARY OF THE INVENTION

An orthopedic clamp includes a pair of clamps mounted on a clamp connector. Each clamp has a variable size opening that varies in size transverse to the bar. At least one of the clamps is longitudinally displaceable relative to the other along the bar, and lockable in its spaced apart position. At least one clamp can also be independently rotated relative to the bar and locked in its rotated position. The first and second clamps are preferably made from radiolucent plastic, whereas the connector bar is preferably made from metal.

Each pair of clamp includes a first clamping arm and a second clamping arm. The first and second arms each include a proximal mounting end and a distal clamping end. The mounting ends area mounted on an axle so that the second arm is rotatable relative to the first arm about an axis, and upon such rotation the distal clamping ends are consequently moved farther away and closer together from each other. Preferably a spring applies a force between the first and second arms to bias the first and second arms away from each other into an open configuration adapted to receive a portion of fractured bone. A rotatable connector extends between the first and second arms, and more preferably through an axis of the spring, and can be rotated to draw the first and second arms toward each other counter to the bias of the spring into an at least partially closed configuration in which the first and second arms are adapted to grip the bone or maintain reduction of a bone fracture.

The clamp device is highly adjustable and compact. The device provides good visibility and access to the wound. In addition, the plastic clamps have low manufacturing costs, and render the clamp device suitable as a single-use device.

BRIEF DESCRIPTION OF THE DRAWINGS

FIG. 8 is an end view of one clamp of the clamp device of FIG. 7.

FIG. 9 is a cross-section through line 9-9 in FIG. 8.

FIG. 10 is an assembly view of the clamp shown in FIG. 8.

DETAILED DESCRIPTION OF THE PREFERRED EMBODIMENTS

Figure 1:
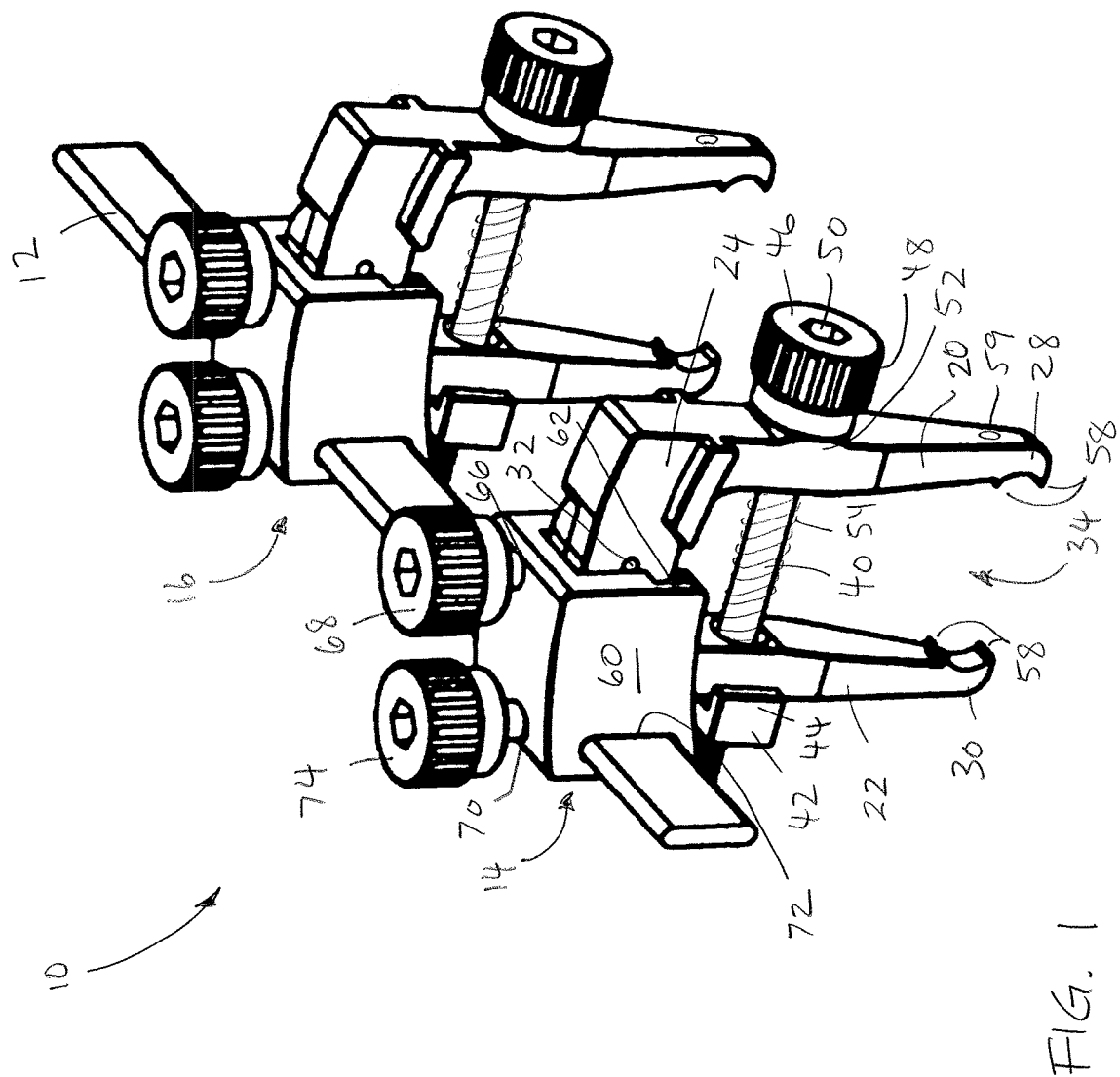
FIG. 1 is a perspective view of an orthopedic clamp device described herein.

Referring to FIGS. 1 through 4, an orthopedic clamp device 10 for maintaining fracture reduction is shown. The clamping device 10 generally includes a clamp connector 12, and first and second clamps 14, 16 displaceable relative to each other along the clamp connector.

The clamp connector is a rigid bar 12. As shown, the bar 12 preferably has a non-circular cross-section, and more preferably a generally rectangular cross-sectional shape. The rectangular cross-section has a height greater than a width, with the width extending substantially parallel to the variable opening within each of the first and second clamps 14, 16. The clamp connector 12 is made of a biocompatible stiff and rigid material.

The first and second clamps 14, 16 are preferably longitudinally displaceable relative to each other along the clamp connector 12, and lockable in respective spaced-apart positions, as described below. The first and second clamps 14, 16 preferably have a common construction. Therefore, clamp 14 will be described as follows, with it understood that clamp 16 preferably comprises like elements and assembly and has all the adjustability of clamp 14, as described below.

Clamp 14 includes first and second clamping arms 20, 22. The first and second clamping arms 20, 22 each include a proximal mounting end 24, 26 and a distal clamping end 28, 30. The clamping arms 20, 22 are preferably movable relative to each other about an axis of a pivot pin 32 at their mounting ends 24, 26 to rotate the clamping ends 28, 30 into a variable sized opening 34 of any dimension between maximum open and fully closed configurations. Exemplar maximum open dimensions include 10-50 mm; such range of maximum sizes may be supported by a single clamp or clamps of different size. The clamp 14 is oriented to the clamp connector 12 such that the size of opening 34 varies in a dimension transverse to the bar 12. Opposed first and second holes 36, 38 are provided in the arms 20, 22, and a bolt 40 extends through the first and second holes. The holes 36, 38 have widthwise minor diameter substantially similar to the bolt 40, and a heightwise major diameter that is slightly larger to permit clearance for rotation of the first and second clamping arms 20, 22 relative to each other over the bolt 40. By way of example, the major diameter may be approximately 20±5 percent greater in dimension that the minor diameter. A nut 42 is rotationally fixed relative to the second clamping arm 22 to facilitate advancement of the bolt 40 therethrough. The rotational fixation may include arms 44 on the nut 42 that extend about the sides of the second clamping arm 22 or, alternatively, can include other means, by way of example, insertion of a non-circular nut into a rotationally interfering recess. The bolt 40 includes a threaded shaft portion 46, and a knurled head 48 and a hex socket 50, both to further facilitate its manual and/or mechanical rotation relative to the first clamping arm 20 and the nut 42. The threads 46 on the bolt are preferably 8-32 or 6-32, which permit fine adjustment. Manual rotation of the head 48 is preferred so that the user feels the pressure imparted on the bone when clamping for tactile feedback. The first arm 20 about the first hole 36 has a convex surface 52 so that as the first and second clamping arms 20, 22 are rotated relative to each other between open and closed configurations, the first arm 20 has a consistently curved surface against which the head 48 makes tangential contact. A spring 54 is provided to apply a force between the first and second clamping arms 20, 22 to bias the arms toward the open configuration. The spring 54 is preferably a compression spring extending coaxially over the bolt 40 and seating at each of its ends in recesses 56 at the insides of the first and second holes 36, 38. The clamping ends 28, 30 of the first and second clamping arms 20, 22 include one or more teeth 58 to engage a bone and bone fragments so that the clamping arms 20, 22, when moved toward the closed configuration about the bone, can apply sufficient force against the bone fragments to maintain grip on bone or to maintain reduction of a bone fracture. A clearance of preferably 15-50 mm is provided from the distal tooth 58 to the bolt 40. The clamping ends 28, 30 may also include angled slots 59 sized to receive auxiliary fixation devices such as K-wires or screws therethrough.

The first and second clamping arms 20, 22 of clamp 14 are coupled to the clamp connector 12 via a mounting bracket 60. The mounting bracket 60 includes a curved internal guide channel 62 that receives curved tracks 64 extending laterally from the second clamping arm 22. The second clamping arm 22 can be advanced into and out of the guide channel to modify the angle at which the entire first clamp 14 is oriented relative to the clamp connector 12. The second clamping arm 22, and thus the clamp 14, can preferably be rotated within a 20° to 45° arc relative to the clamp connector 12, although other angular displacements are possible. A first threaded hole 66 is provided in the mounting bracket 60 into communication with the guide channel 62, and a first set screw 68 with manual knob is coupled within the first threaded hole 66. The first set screw 68 can be released to permit to the second clamping arm 22 to ride within the guide channel 62, and rotated into contact with the second clamping arm to fix the position of the second clamping arm relative to the mounting bracket, and thus the angle of the first clamp 14 relative to the clamp connector 12. A second threaded hole 70 is provided in the mounting bracket into communication with a slot 72 that receives the clamp connector 12, and a second set screw 74 with manual knob is coupled within the second threaded hole. The second set screw 74 can be released to permit longitudinal movement of the mounting bracket 60 over the clamp connector 12 to displace the first clamp 14 relative to the second clamp 16; the second set screw 74 can then be rotated into contact with the clamp connector 12 to fix the position of the first clamp 14 relative to the second clamp 16. The first and second clamps 14, 16 are preferably capable of being moved within 25 mm of each other, and preferably at least 100 mm apart from each other along the clamp connector 12.

The rotational displacement of the first and second clamping arms 20, 22 of each of the first and second clamps 14, 16, the angular displacement of the first and second clamps 14, 16 relative to their mounting bracket 60 and the clamp connector 12, and the longitudinal displacement of the first and second clamps 14, 16 along the clamp connector 12 provide excellent configurability and adaptability to many bones and fracture conditions. The opening clearance 34 within the first and second clamps 14, 16 provides ample working space to manipulate bone reduction and insert and provide at least temporary fixation of a fracture fixation plate 76 onto the bone 78 without removal of the clamping device 10 (FIG. 5).

Figure 2:
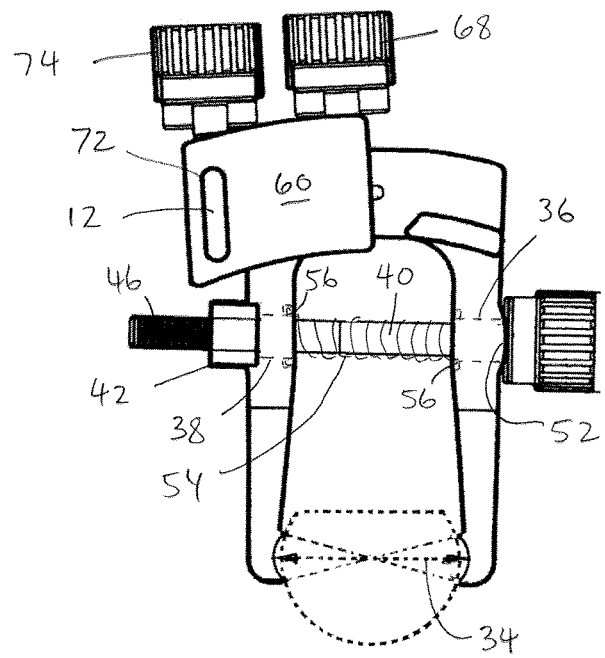
FIG. 2 is an end view of the orthopedic clamp device of FIG. 1.
Figure 3:
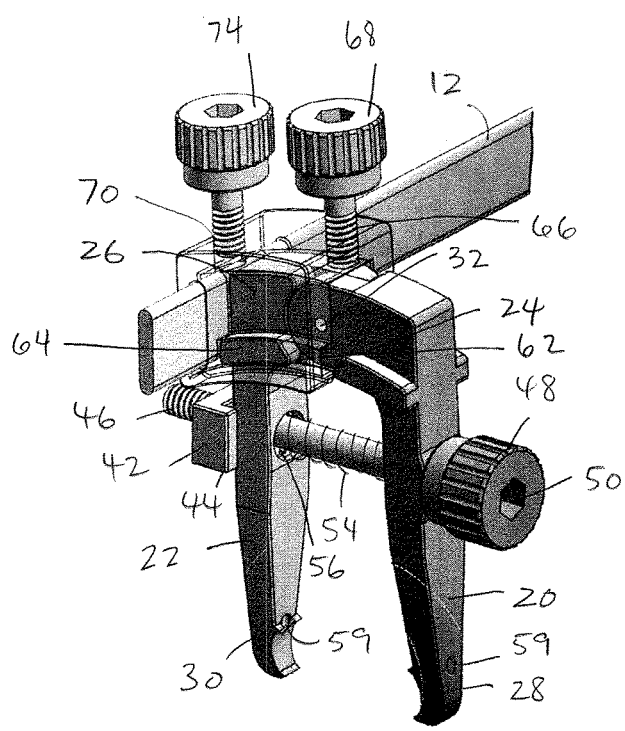
FIG. 3 is a broken, partial transparent, perspective view of the orthopedic clamp device of FIG. 1.
Figure 4:
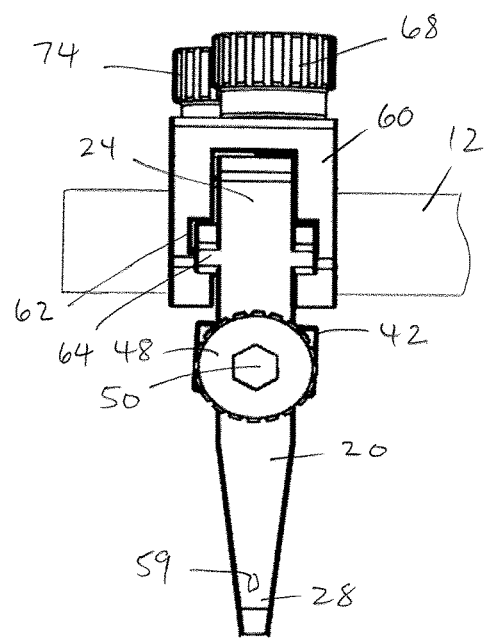
FIG. 4 is a broken second side view of the orthopedic clamp device of FIG. 1.
Figure 5:
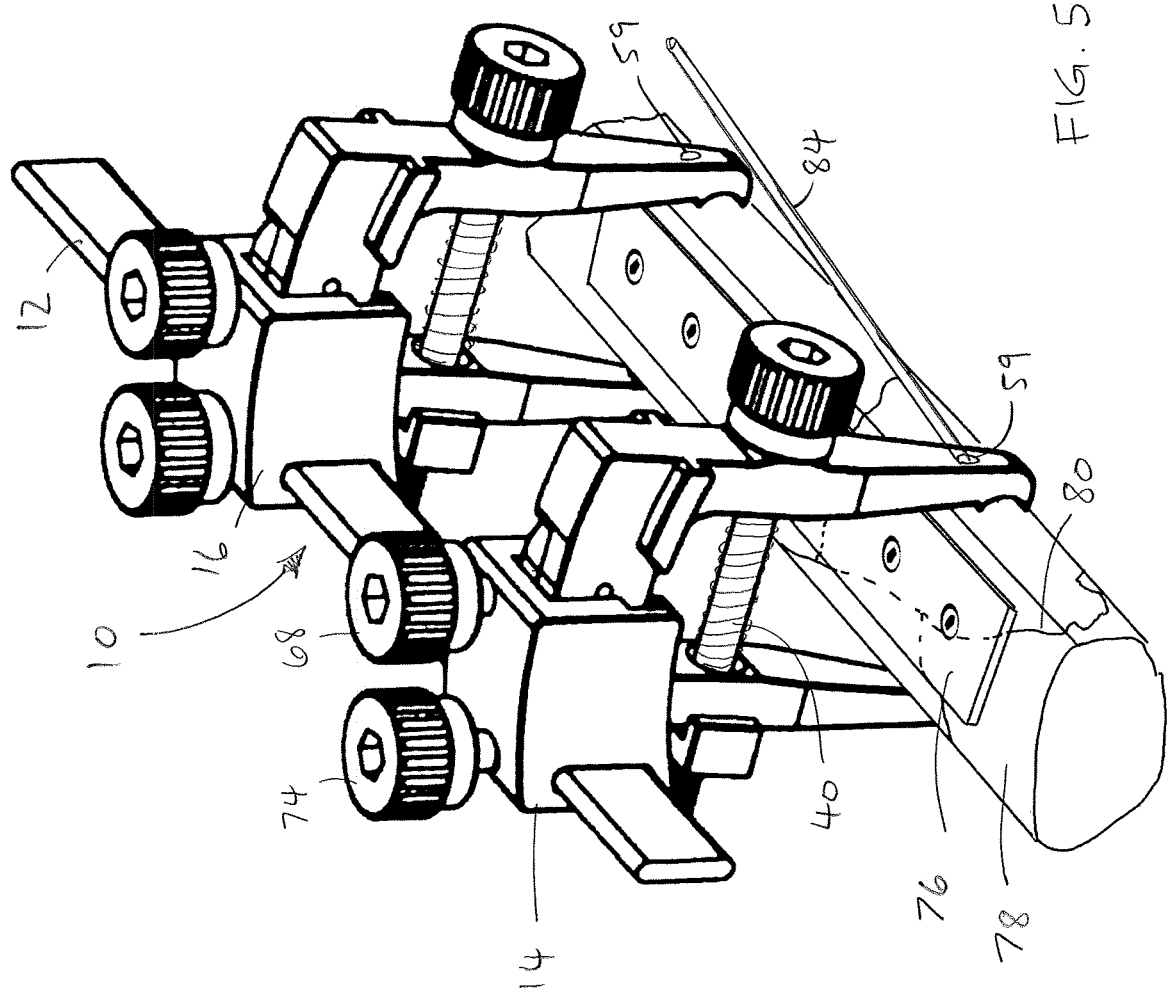
FIG. 5 is a perspective view of the orthopedic clamp device of FIG. 1, as applied to a fracture bone to retain reduction of the fracture while a bone plate is implanted.

Referring to FIGS. 2 and 5, in use, the bolts 40 are loosened to permit the clamps 14, 16 to have openings 34 of sufficient dimension to be received over the bone 72. The first and second screws 68, 74 are also loosened to permit relative angular and longitudinal adjustment of the clamps 14, 16 relative to each other. The fracture 80 is reduced. The clamping device 10 is positioned onto the bone 78, with each clamp 14, 16 located to hold the reduction. The loosened first and second screws 68, 74 allow the clamps 14, 16 to be moved to an appropriate longitudinal and angular displacement to maintain the reduction. The bolt 40 on each clamp 14, 16 is sufficiently tightened to cause their clamping arms 20, 22 to retain the reduction without providing excess compression that would displace bone fragments or otherwise operate counter to the procedure. The first and second screws 68, 74 are securely tightened to maintain the set configuration. One or more bone fixation devices 84 may be inserted through holes 59 in the lower clamping ends of the clamping arms 20, 22 and into bone therebetween for temporary stability of the bone. Then, the plate 76 can be positioned between the clamping arms 20, 22, under the bolt 40, and onto the bone 78. While the reduction is maintained with the clamping device 10, the plate 76 is at least partially, and optionally fully secured to the bone. The fixation devices 84, if used, are then removed. Then, the bolts 40 of the clamps 14, 16 are loosened, allowing the arms 20, 22 of each clamp to spread apart, and the clamping device 10 is removed.

In accord with one preferred, though not required, aspect of the clamp 10, the first and second clamping arms 20, 22 of each clamp 14, 16 are hermaphroditic, and all features described with respect to either the first or second arms 20, 22 are likewise provided to the other, such a configuration being shown in the figures. In this manner, a single arm construct may be utilized for assembly of both of the first and second clamping arms.

The first and second clamping arms 20, 22 of each clamp 14, 16 and mounting brackets 60 may be made from a plastic, such as a transparent or translucent, radiolucent, polycarbonate which provides enhanced viewing of the bone 78 both visually to the surgeon and under fluoroscopy as a surgical procedure is being performed thereon. Alternatively, the clamps 14, 16 may be made from other polymers, including nylon or glass-filled polymers with high stiffness. Polymeric materials are lighter and provide a less massive and more manageable instrument. Further, such a device is readily adapted from a manufacturing cost perspective to be a single-use, disposable instrument. As yet another alternative, the clamps may be made from a metal. The remaining components of the clamping device 10, including the clamp connector 12, bolts 40, screws 68, 74, nuts 42, and springs 54, may be made from a suitable metal, such as a stainless steel, a suitable plastic, or a combination thereof.

Figure 6:
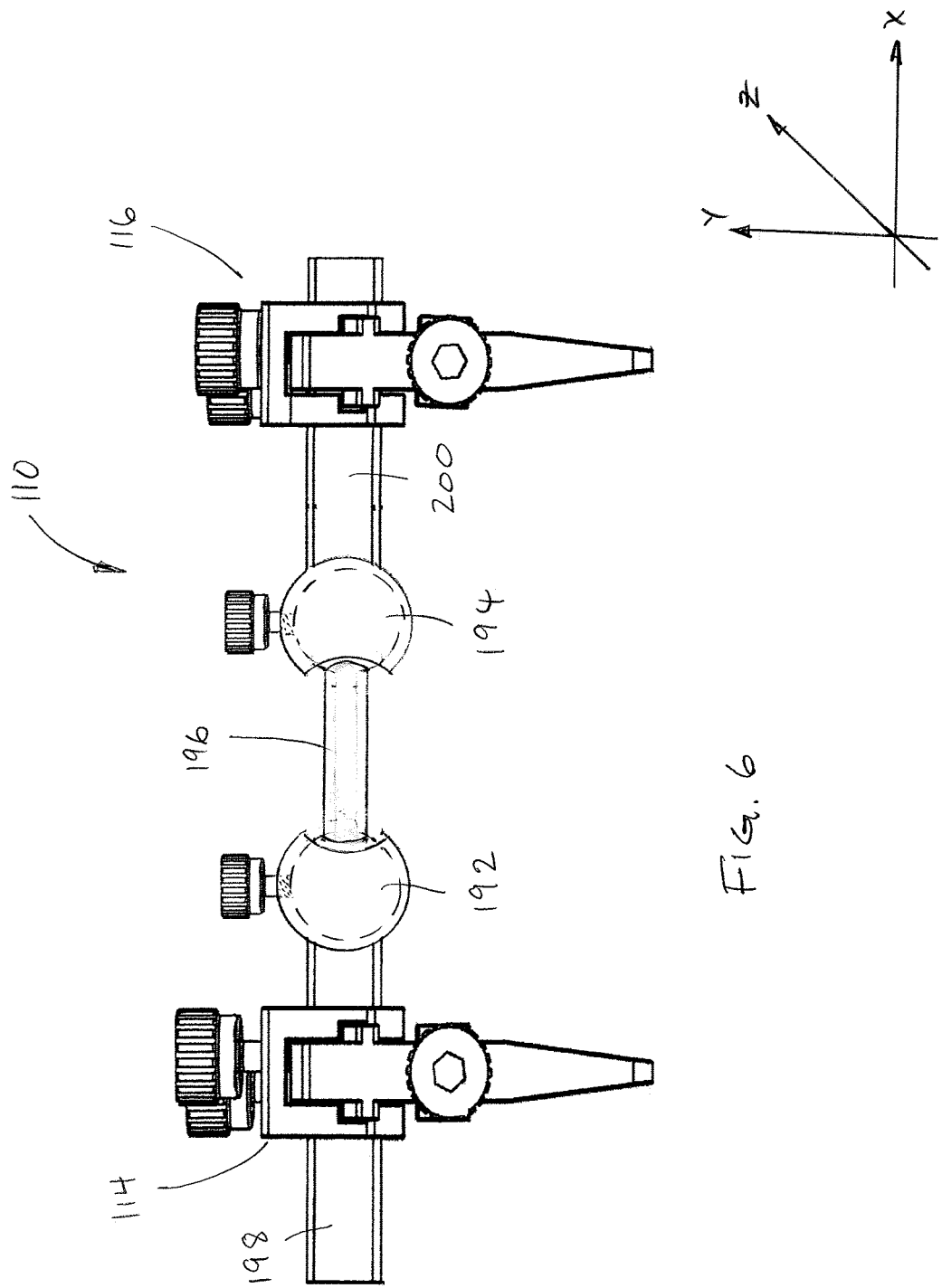
FIG. 6 is a side elevation view of another embodiment of an orthopedic clamp device.

Turning now to FIG. 6, another embodiment of a universal clamp device 110 for use on bone, substantially similar to the clamp 10 (with like parts having reference numerals incremented by 100) is shown. The clamp connector 112 includes an articulation system 190 between the clamps 114, 116. The articulation system 190 includes at least one, and preferably two, universal joints 192, 194, and an articulation bar 196 between the ball joints. Each joint 192, 194 permits displacement of the clamps 114, 116 along x-, y- and z-axes relative to each other. The use of both joints 192, 194 together permits the clamps 114, 116 to be displaced along parallel, non-coaxial axes. While joints 114, 116 are shown as ball joints, other suitable joints and mechanisms permitting the described displacement can also be used. The clamps 114, 116 remain longitudinally displaceable along each of first and second portions 198, 200 of the clamp connector. Alternatively, one of the clamps 114, 116 may be longitudinally fixed to one of the joints 192, 194, with all longitudinal displacement occurring at the other end of the clamp device 110.

Figure 7:
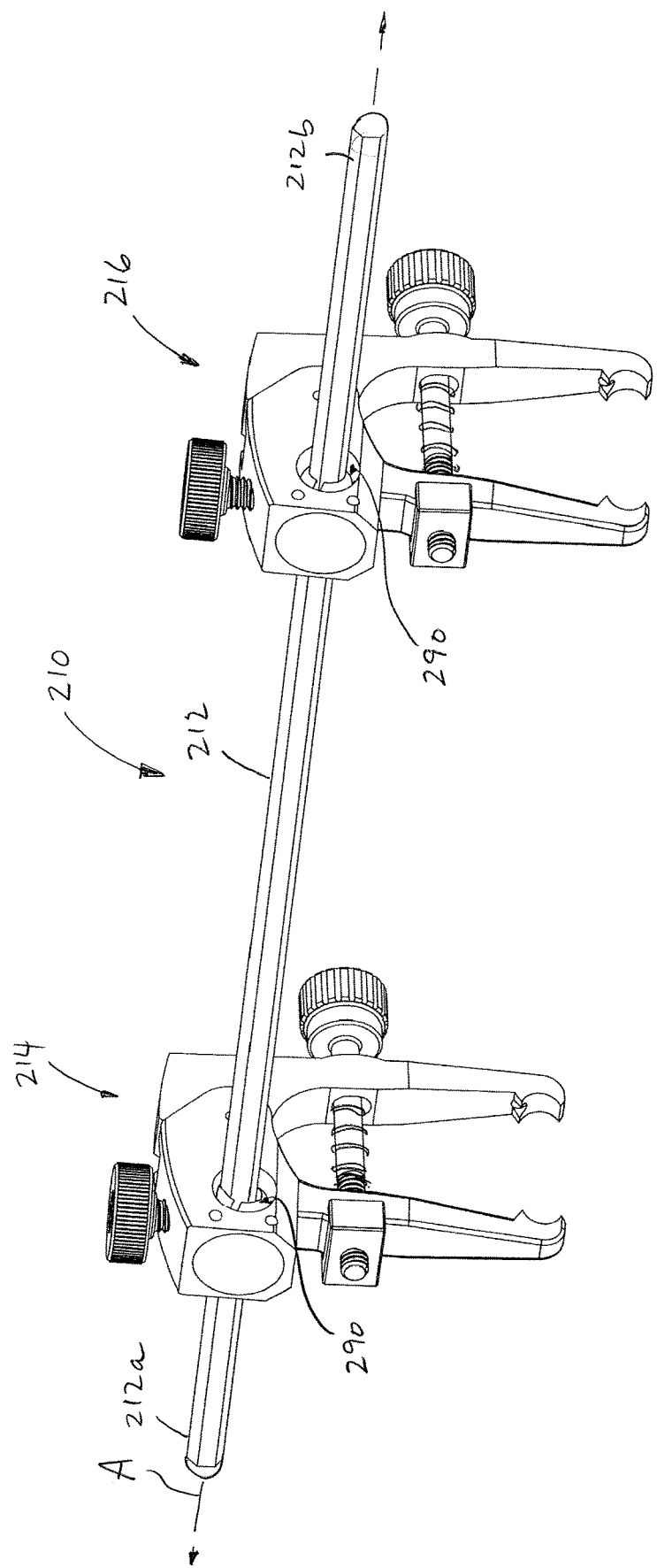
FIG. 7 is a perspective view of another embodiment of an orthopedic clamp device.

Turning now to FIG. 7, another embodiment of universal clamp device 210 for use on bone (with like parts relative to device 10 having reference numerals incremented by 200) is shown. Each clamp 214, 216 includes an integrated articulation system 290 that permits angular and rotational displacement of the clamp connector 212 relative to the respective clamp 214, 216. The articulation system 290 is preferably a universal or ball joint that is adapted to provide a limited range of motion of the respective clamp 214, 216 on the clamp connector 212, e.g., at least ±15°, and more preferably ±30°, relative to a normal axis A to a plane of the respective clamp 214, 216. In FIG. 7, the connector bar 212 is coaxial with the normal axis A.

Referring to FIGS. 8 through 10, in an embodiment, the articulation system 290, described with respect to clamp 214, includes an opening 292 formed in the upper end of clamp arm 222. Opening 292 includes an inner first portion 294 defining a flat 293 and a spherical surface 295 forming a portion of a socket for a ball structure 296, an outer cylindrical bore portion 298, transverse openings 300, 302 for passage of the clamp connector 212, and an upper threaded bore 303. A socket insert 304 defining a flat 305 and a spherical surface 306 forming a remainder of the socket for the ball structure 296 is provided into the bore portion 298 and captures the ball structure 296. The socket inert 304 insert is captured and retained with pins 308 fixed in clamp arm holes 309 and insert holes 311 (FIG. 10). The ball structure 296 comprises upper and lower generally hemispherical elements 310, 312 which together define an axial passage 314 for the clamp connector 212 and lateral flats 316, 318 (FIGS. 9 and 10). Hemispherical elements 310, 312 may be free floating within the socket, or may be retained in a spaced apart configuration, e.g., with one or more spring elements (not shown). The lateral flats 316, 318 face corresponding flats 293, 305 on the first portion 294 and the socket insert 304, but are slightly spaced apart therefrom in a neutral position. However, the facing flats 293, 316, and 305, 318 interfere when the ball structure 296 is laterally angularly displaced by more than a predetermined amount, such as 15° from normal, to function as a stop for maximum angular displacement.

Figure 11:
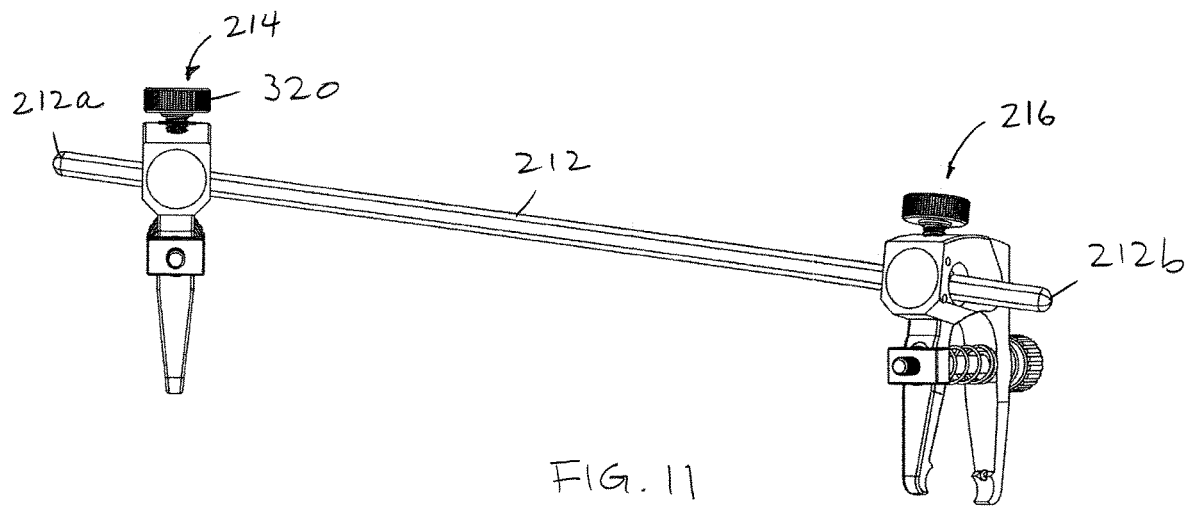
FIG. 11 is a side elevation of an assembled clamp device with first and second clamps angularly offset relative to each other.
Figure 12:
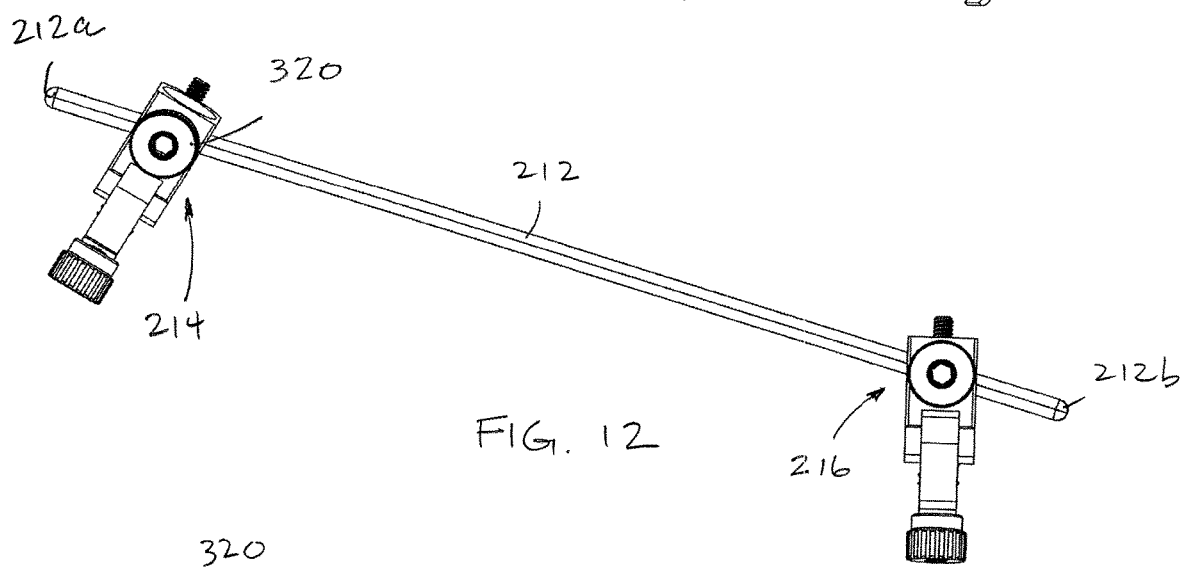
FIG. 12 is a top view of the clamp device in the orientation of FIG. 11.
Figure 13:
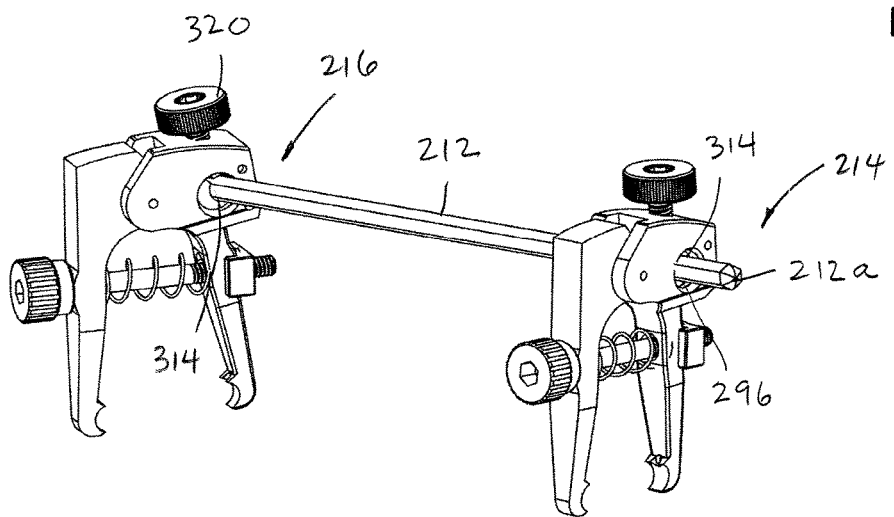
FIG. 13 is an end perspective view of the clamp device in the orientation of FIG. 11.
Figure 14:
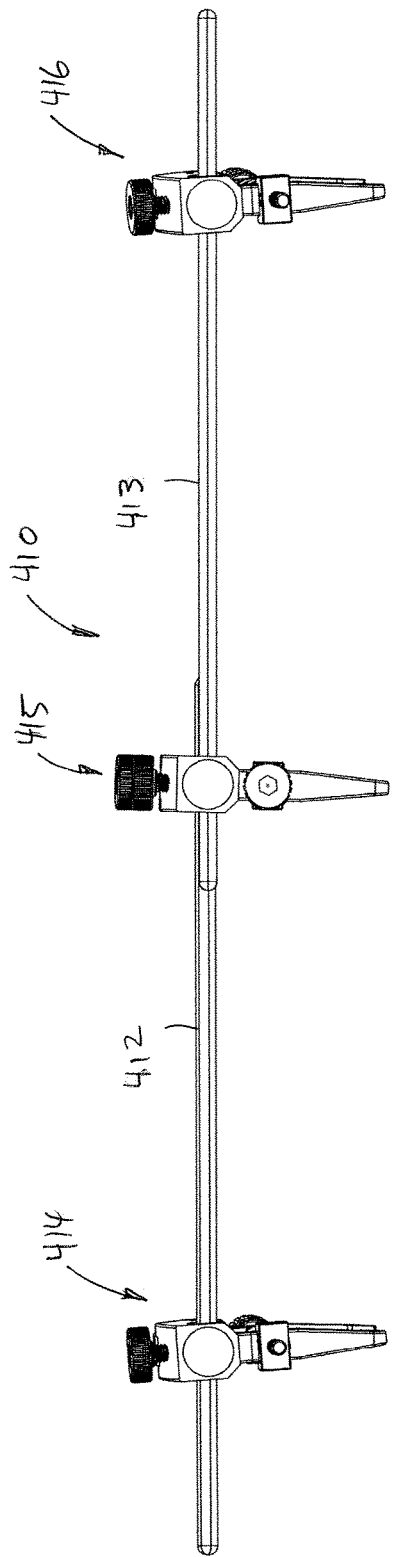
FIG. 14 is a side elevation of an assembled clamp device with three clamp angularly offset relative to each other.
Figure 15:
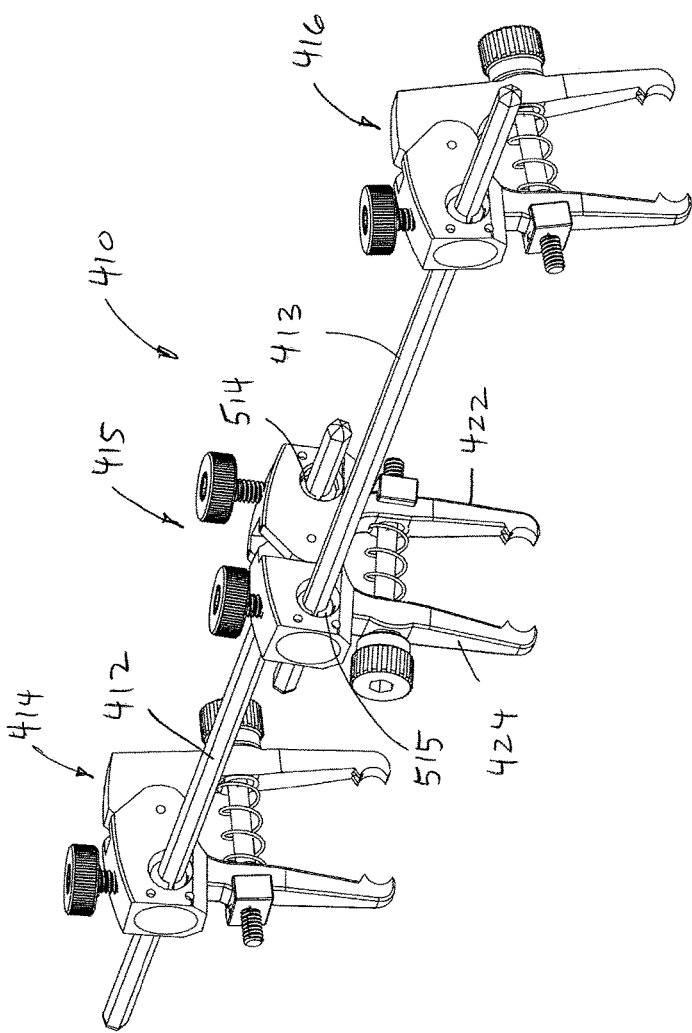
FIG. 15 is a perspective view of the clamp device in the orientation of FIG. 14.

Referring now to FIGS. 8 through 13, the clamp connector 212 is positioned through the axial passages 314 of both clamps 214, 216. The ends 212a, 212b of the clamp connector 212 may be rounded or otherwise tapered to facilitate insertion through the axial passage 314. The axial passages 314 may be defined as round (as shown) or optionally the clamp connector 212 and axial passages 314 may have interfering cross-sectional shapes, e.g., square or hexagonal, such that relative rotation between the clamp connector 212 and the ball structure 296 of the clamps 214, 216 is prohibited. A locking screw 320 is inserted into the threaded bore 303 and can be advanced to tighten the ball structure 296 about the clamp connector 212 and lock the ball structure 296 relative to the clamp 214; or loosened to permit repositioning of the ball structure 296 along the clamp connector 212 and/or the angular position of the clamp 214 relative to the ball structure. FIGS. 11 through 13 show the clamps angularly displaced relative to each other. The clamp device can also be used with more than two clamps and more than two clamp connectors. Turning now to FIGS. 14 and 15, an assembly of a device 410 is shown using three clamps 414, 415, 416 and two clamp connectors 412, 413. Clamps 414, 416 include, as described above with clamps 14, 114 and 214, a socket or other structure at one side of the clamp in which to receive a clamp connector. However, clamp 415 is a double-connecting clamp, including a socket 514, 515 or suitable structure in which to receive clamp connectors 412, 413 at both sides of the clamp; i.e., in each clamp arm 422, 424. Likewise, clamps 414 and/or 416 can be replaced with double-connecting clamps, such that additional clamp connectors can be added to assemble a clamping device of appropriate length for a procedure. Moreover, where a double-connecting clamp is utilized, other clamps need not independently articulate relative to the clamp connectors to which they are attached is order to have a high degree of adjustment for most applications.

There have been described and illustrated herein embodiments of a bone clamping device and methods of using the same. While particular embodiments of the invention have been described, it is not intended that the invention be limited thereto, as it is intended that the invention be as broad in scope as the art will allow and that the specification be read likewise. Thus, while the bone clamping device has been described in one use for fracture reduction, its use is not limited by the description herein, as it may also be used for bone stabilization during osteotomies and arthrodesis. Further, while particular the clamp connector is disclosed as a single bar, it will be appreciated that the clamp connector may comprise one or more rigid longitudinal elements extending between clamps, and may be round, circular, oval, rectangular, square or other shape in cross-section. In addition, while the bolt and spring are shown in an embodiment to be coaxial, they may be otherwise configured and even otherwise spaced apart. Also, while the knobs effecting and releasing longitudinal fixation of the clamps along the clamp connector are shown positioned at the upper side of the clamping device, the knobs may be provided along a lateral or lower side of the clamping device. Further, while the knobs effecting and releasing angular fixation of the first and second arms of the clamps are shown positioned at the upper side of the clamping device, the knobs may be provided along a lateral side of each clamp. Also, while various materials have been disclosed for manufacture of the clamping device, other suitable materials can be used and may be appropriate depending on whether the clamping device is intended as a single-use disposable or multi-use re-usable surgical device. Moreover, the clamping device may be provided in various sizes so as to be adapted to maintain reduction on bones of different portions of the human body, on human bodies of different size, and even non-human mammalian and other animal bodies. It will therefore be appreciated by those skilled in the art that yet other modifications could be made to the provided invention without deviating from its scope as claimed.

What is claimed is:

1. A bone clamping device for stabilizing one or more bones, comprising:
    a) a first clamp having first and second opposing clamping arms which are adapted to receive a bone therebetween, the first and second clamping arms rotatable about a first axis, wherein the first and second clamping arms of the first clamp are biased apart with a spring;
    b) a second clamp having first and second opposing clamping arms which are oriented and adapted to also receive the bone therebetween, the first and second clamping arms of the second clamp rotatable about a second axis;
    c) a clamp connector having a fixed length, the first and second clamps provided on the clamp connector, the clamp connector laterally offset from each of the first and second axes, wherein
        at least one of the first and second clamps is longitudinally displaceable relative to the other along the clamp connector, and lockable in a spaced apart position from the other of the first and second clamps, and
        at least one of the first and second clamps is independently rotatable within an arc relative to the clamp connector and lockable relative to the clamp connector in its rotated position; and
    d) a mounting element that connects the first clamp to the clamp connector, the mounting element having a curved channel, and the first clamp having at least one lateral track that is displaceable through the channel to modify the angle at which the first clamp is arranged relative to the clamp connector.

2. The bone clamping device of claim 1, wherein:
the first clamp includes a movable element that draws the first and second clamping arms of the first clamp together counter to the bias of the spring.

3. The bone clamping device of claim 1, wherein:
the spring extends coaxial with the movable element.

4. The bone clamping device of claim 1, further comprising:
    a set screw that extends into the hole in the mounting element and engages the first clamp to lock a position of the first clamp relative to the mounting element.

5. The bone clamping device of claim 1,
wherein the mounting element has a slot through which the clamp connector is longitudinally displaceable, and screw hole intersecting the slot, and
    a set screw that extends into the screw hole engages the clamp connector to lock a position of the first clamp relative to the clamp connector.

6. The bone clamping device of claim 1, wherein:
the first and second clamping arms of the first clamp are coupled together at respective mounting ends and displaceable from each other at respective clamping ends, the clamping ends each having at least one tooth to engage bone.

7. The bone clamping device of claim 6, wherein:
at least one of the clamping ends includes a hole adapted to receive a bone fixation device.

8. The bone clamping device of claim 1, wherein:
the clamp connector is articulable between the first and second clamps.

9. A bone clamping device according to claim 1, wherein:
the clamp connector is rigid and has a third axis, wherein the first and second clamping arms of the first clamp open and close to define a variable space extending in a clamping direction, and the third axis is offset from the first and second axes relative to said clamping direction.

10. The bone clamping device of claim 1, wherein:
the clamp connector is made from metal, and the first and second clamps are made from plastic.

11. The bone clamping device according to claim 1, wherein the first and second clamps are made from plastic.

12. The bone clamping device of claim 11, wherein:
the first and second clamps are made from a transparent or translucent material.

13. The bone clamping device of claim 11, wherein:
the first and second clamps are made from a radiolucent material.

14. The bone clamping device of claim 11, wherein:
the clamp connector is articulable between the first and second clamps.

15. A bone clamping device for stabilizing one or more bones, comprising:
    a) a first clamp having first and second opposing clamping arms which are adapted to receive a bone therebetween, the first and second clamping arms rotatable about a first axis;
    b) a second clamp having first and second opposing clamping arms which are oriented and adapted to also receive the bone therebetween, the first and second clamping arms of the second clamp rotatable about a second axis; and c) a clamp connector having a fixed length, the first and second clamps provided on the clamp connector, the clamp connector laterally offset from each of the first and second axes, wherein at least one of the first and second clamps is longitudinally displaceable relative to the other along the clamp connector, and lockable in a spaced apart position from the other of the first and second clamps, and at least one of the first and second clamps is independently rotatable within an arc relative to the clamp connector and lockable relative to the clamp connector in its rotated position, wherein:

the first clamp includes a first universal joint at which the first clamp is adapted to articulate relative to the clamp connector, the first clamp having a lock that locks the first clamp in a respective position relative to the clamp connector.

16. The bone clamping device of claim 15, further comprising:

a second clamp connector, wherein, the first clamp includes a second universal joint at which the first clamp is adapted to articulate relative to the second clamp connector, the first clamp having a lock that locks the first clamp in a respective position relative to the second clamp connector.

17. The bone clamping device of claim 16, wherein:

the second clamp includes a third universal joint at which the second clamp is adapted to articulate relative to one of the second clamp connector, the second clamp having a lock that locks the second clamp in a respective position relative to the second clamp connector.

18. The bone clamping device of claim 15, wherein:

the first universal joint includes a stop that limits the maximum articulation of the first clamp relative to the clamp connector.

19. The bone clamping device of claim 15, wherein:

the first universal joint is integrated within the first clamping arm of the first clamp.

20. The bone clamping device of claim 19, wherein:

the first universal joint includes a socket at least partly defined by the first clamping of the first clamp, and a ball element rotatable within the socket, the ball element having a passage through which the clamp connector is received.

21. The bone clamping device of claim 15, further comprising:

a third clamp having first and second opposing clamping arms which are oriented and adapted to receive bone therebetween, the first and second clamping arms of the third clamp rotatable about a third axis, the third clamp coupled to the clamp connector.

22. A bone clamping device for stabilizing one or more bones, comprising:

a) a first clamp having first and second opposing clamping arms rotatable about a first axis and adapted to receive a bone therebetween, a first universal joint having a first socket at least partly defined by the first clamping arm of the first clamp, a first ball element rotatable within the first socket, the first ball element defining a first passage, a first lock configured to lock the position of the clamping arms of the first clamp relative to one another, and a second lock separate from the first lock;

b) a second clamp having first and second opposing clamping arms rotatable about a second axis and adapted to receive the bone therebetween, a second universal joint having a second socket at least partly defined by the first clamping arm of the second clamp, a second ball element rotatable within the second socket, the second ball element defining a second passage, a third lock configured to lock the position of the clamping arms of the second clamp relative to one another, and a fourth lock separate from the third lock; and c) a clamp connector extending through the first and second passages and longitudinally displaceable within, wherein the second and fourth locks are configured to independently lock the position of the first and second ball elements within the first and second sockets, respectively, and the longitudinal position of the clamp connector relative to each of the first and second clamps.

23. A bone clamping device according to claim 22, wherein:

the clamp connector is rigid and has a third axis, wherein the first and second clamping arms open and close to define a variable space extending in a clamping direction, and the third axis is offset from the first and second axes relative to said clamping direction.

24. The bone clamping device according to claim 22, wherein the first clamp is adapted to articulate relative to the clamp connector at the first universal joint, and wherein the second lock locks the first clamp in a respective position relative to the clamp connector, wherein the second clamp is adapted to articulate relative to the clamp connector at the second universal joint, and wherein the fourth lock locks the second clamp in a respective position relative to the clamp connector.

25. A bone clamping device for stabilizing one or more bones, comprising:

a) a first clamp having a first clamping arm and a second clamping arm rotatable relative to the first clamping arm about a first clamp axis;

b) a second clamp having a first clamping arm and a second clamping arm rotatable relative to first clamping arm of the second clamp about a second clamp axis;

c) a clamp connector;

wherein the first clamp is mounted to the clamp connector via a first mounting bracket, separate from the second clamping arm, that rides on, and is displaceable relative to, a surface of the second clamping arm of the first clamp, the second clamp is mounted to the clamp connector via a second mounting bracket, separate from the second clamping arm, that rides on, and is displaceable relative to, a surface of the second clamping arm of the second clamp, the second mounting bracket is longitudinally displaceable and lockable in a spaced apart position relative to the first mounting bracket along the clamp connector, and the first clamp is independently rotatable on the first mounting bracket and relative to the clamp connector so that the first clamp axis is offset from the second clamp axis.

26. The bone clamping device of claim 25, further comprising:

a first spring biasing apart the first and second clamping arms of the first clamp, and a second spring biasing apart the first and second clamping arms of the second clamp.

27. The bone clamping device of claim 25, wherein:
the clamp connector is made from metal, the first and second clamps are made from plastic.

28. A bone clamping device for stabilizing one or more bones, comprising:
   a) a clamp connector;
   b) a first clamp having first and second clamping arms, wherein the first and second clamping arms of the first clamp each have a mounting end and a clamping end, and are rotatable relative to each about an axis; and
   c) a second clamp having first and second clamping arms, wherein
      at least one of the first and second clamps is displaceable relative to the other along the clamp connector, and lockable in a spaced apart position from the other of the first and second clamps, and
      at least the first and second clamping arms of the first clamp are spring biased apart from each other by a spring and movable against the spring bias with a rotatable element that extends between the first and second clamping arms and drives the first and second clamping arms toward one another, wherein the rotatable element extends from the first clamping arm to the second clamping arm between the axis and the clamping ends.

29. The bone clamping device of claim 28, wherein:
the spring and rotatable element are coaxial.

30. The bone clamping device of claim 28, wherein:
15 to 50 mm of space is defined between the clamping ends and the rotatable element.

31. The bone clamping device of claim 28, wherein:
the clamp connector is made from metal, and the clamping arms of the first and second clamps are made from plastic.

* * * * *